(12) United States Patent
Dabal

(10) Patent No.: US 6,398,720 B1
(45) Date of Patent: Jun. 4, 2002

(54) PENILE SIZE ENHANCEMENT DEVICE AND METHOD

(76) Inventor: Peter Dabal, 148 W. 68th St., #3D, New York, NY (US) 10023

( * ) Notice: Subject to any disclaimer, the term of this patent is extended or adjusted under 35 U.S.C. 154(b) by 0 days.

(21) Appl. No.: 09/500,140

(22) Filed: Feb. 8, 2000

(51) Int. Cl.⁷ .................................................. A61F 5/00
(52) U.S. Cl. ....................................................... 600/38
(58) Field of Search ..................................... 600/38–41

(56) References Cited

U.S. PATENT DOCUMENTS

| | | | | |
|---|---|---|---|---|
| 4,628,914 A | * | 12/1986 | Everson | 600/39 |
| 4,718,411 A | | 1/1988 | Stewart | 128/79 |
| 4,753,227 A | | 6/1988 | Yanuck, Jr. | 128/79 |
| 4,856,499 A | | 8/1989 | Kelly | 128/79 |
| 5,295,946 A | | 3/1994 | Collins | 600/41 |
| 5,501,650 A | | 3/1996 | Gellert | 600/38 |
| 5,536,233 A | * | 7/1996 | Khouri | 600/38 |
| 5,599,275 A | * | 2/1997 | France | 600/38 |
| 5,622,186 A | | 4/1997 | Schwartz | 128/842 |
| 5,707,341 A | | 1/1998 | Mathewuse | 600/39 |
| 5,782,621 A | | 7/1998 | Harris | 417/470 |
| 5,836,864 A | | 11/1998 | Clark, Jr. | 600/38 |
| 5,951,460 A | | 9/1999 | Vollrath | 600/38 |
| 6,036,635 A | * | 3/2000 | Altshuler | 600/38 |

* cited by examiner

Primary Examiner—Eric F. Winakur
Assistant Examiner—Joseph A. Cadugan
(74) Attorney, Agent, or Firm—Christopher Whewell

(57) ABSTRACT

Provided herein is a device useful in causing enlargement of a flaccid penis. The device includes a first and a second semi-bulbular shaped member portions which are hingably connected to one another and closable to form a bulb shaped device having a hollow interior volume. A flaccid penis may be inserted into a device according to the invention and a vacuum is applied to force blood from the subject into the penis, thus causing enlargement of the penis. Methods for use of the device are provide.

10 Claims, 5 Drawing Sheets

PENILE SIZE ENHANCEMENT DEVICE AND METHOD

TECHNICAL FIELD

This invention relates to a device and method for enhancement and enlargement human bodily organs in general, and more particularly to a device and method for enhancing the size of the human penis organ.

BACKGROUND

Erectile dysfunction is known to the medical community and certain males of the human species as a condition under which the penis loses its ability to achieve a sufficiently erect state for the act of insertion of the penis in copulative behavior to be possible. Chemical substance abuse such as alcoholism and old age are but two possible causes for such erectile dysfunction.

It is known that the penis shaft is made up of three cylindrical masses of erectile tissue covered by skin. The erectile tissue masses are composed of large venuous sinusoids or spaces which are fed by blood from arteries and drained by veins. They contain very little blood when the individual is not aroused. When aroused, the arteries pump extra blood to the tissue and the penis enlarges. The veins draining the sinusoids are equipped with constrictor muscles which serve to block off the reverse flow of blood out of the sinusoids during arousal, which causes the sinusoids to become inflamed with blood at arterial pressure. The erectile tissue expands to fill the skin of the penis tightly, resulting in an enlarged an rigid organ.

In many cases of impotence, there is adequate arterial blood supply, but apparently inadequate closing off of the venous channels to inflate the sinusoids to maintain satisfactory rigidity or erection.

The inability of a male to achieve an erect penis ("erection") may in some cases be the cause of psychological strain on a relationship between two persons, since the lack of an erection renders one so afflicted to be unable to engage in sexual activity with a mate. As the inability to perform intimately can destroy a marriage, it would be desirable by those experiencing the inability to achieve an erection to have at their disposal a means for restoring the ability to achieve an erection.

SUMMARY OF THE INVENTION

The present invention is a device useful for assisting in causing an erection in human males. The device in general is contoured to have a bulb-shaped outer surface, and preferably comprises a semi-bulbular first member comprising a semi-circular upper portion, a flat lower portion, and two straight sidewall portions, said sidewall portions angled inwardly from the semicircular upper portion and terminating at said flat lower portion, further comprising a flange portion which circumscribes said sidewall portions and said semi-circular upper portion. The device also comprises a semi-bulbular second member comprising a semi-circular upper portion, a flat lower portion, and two straight sidewall portions, said sidewall portions angled inwardly from the semicircular upper portion and terminating at said flat lower portion, further comprising a flange portion which circumscribes said sidewall portions and said semi-circular upper portion. The first and second members are hingably attached to one another along one of said sidewall portions of each member in such fashion to render the flange of the first member and said flange of the second member to contact one another upon closing the first and said second members. The present invention is thus shaped, in its closed configuration, like a light bulb. Thus, the device of the invention in its closed configuration comprises a bulb-shaped surface. There is at least one hole disposed through the bulb-shaped surface, for receiving a source of vacuum.

DETAILED DESCRIPTION

Figure 1:
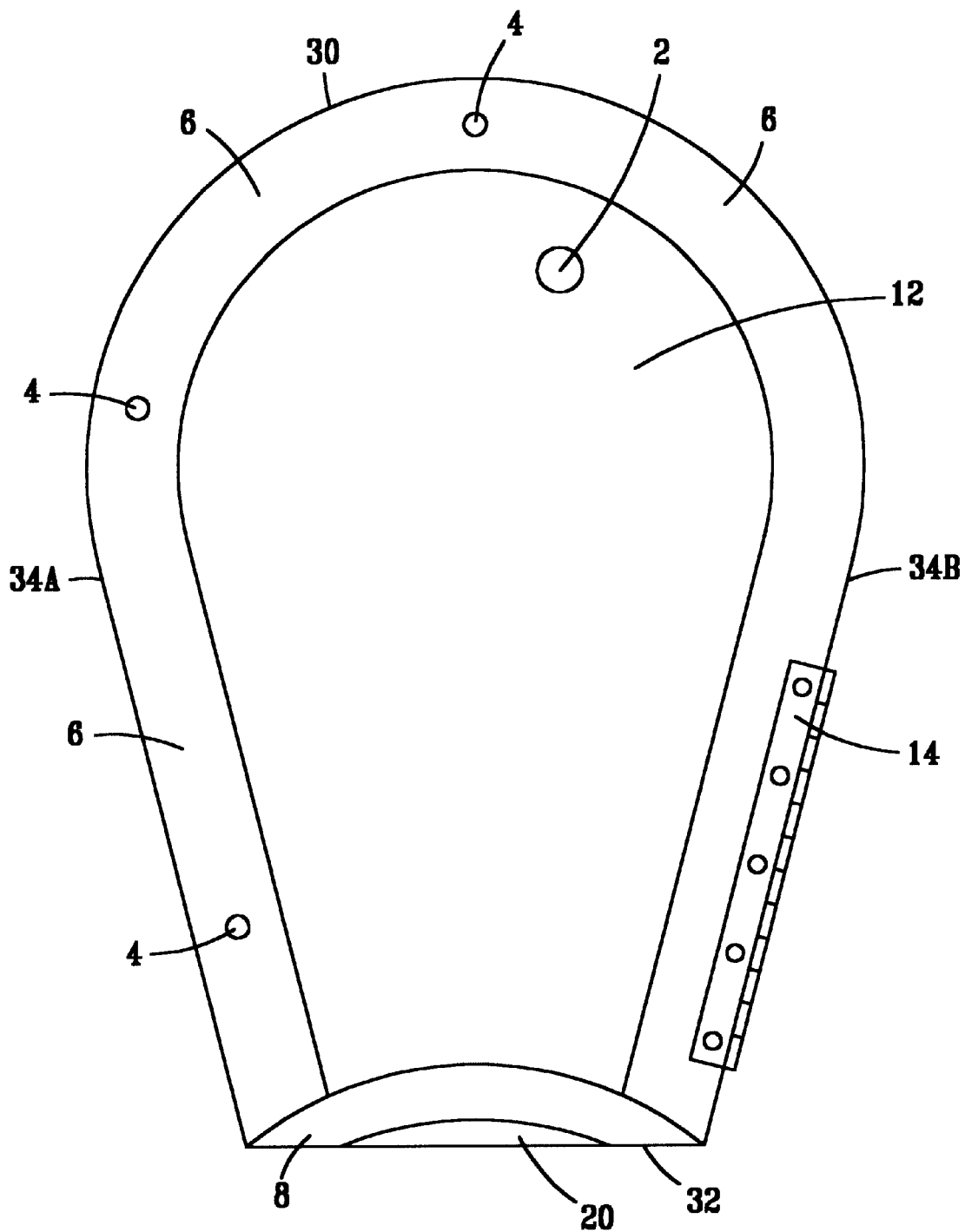
FIG. 1 is a side view of the device of the invention in its closed configuration.

Referring to the drawings and initially to FIG. 1 there is shown a side view of a device according to the invention in its closed configuration. The device comprises two half portions ("members"), which are connected along one of their sides preferably by means of a hinge 14. Thus, the device of the invention may also take on an open configuration, as when the two members are not closed with respect to one another, as is shown in the other figures.

In general terms, the device is bulb-shaped when in its closed configuration by virtue of its being comprised of two semi-bulbular members. It is the closed configuration that is employed when the device is to be used for assisting in the achievement of an erection. The device has a semi-circular upper portion 30, a flat lower portion 32, and sidewall portions 34A and 34B that are angled inwardly from the semicircular upper portion and which terminate at the flat lower portion. Here, the inner volume 12 defined by the outer surfaces of the two members of the invention is shown, which is adapted to receive and contain a human penis. A means for connecting a reduced pressure or vacuum to the inner volume 12 is conveniently provided to the device by providing a hole 2 disposed through the bulb-shaped outer surface 69 (FIG.2) of the device. In this closed configuration of the device, the outer surface is symmetrical about the longitudinal axis of the device. There is a flange portion 6, which as otherwise described herein circumscribes the outer portion of the bulb surface, thus rendering the flange portion to take on the shape of a horseshoe. Disposed along the flange portion are a plurality of holes 4, which are useful for providing a means for holding the two members from which the device is preferably constructed in a closed configuration. The invention includes a lip portion 8, which in the closed configuration of the device is coextensively disposed about the flat lower portion as is later shown in more detail in FIG. 5. The lip on the flat lower portion is shaped to fit up against the pubic bone of the subject using the device, to form a seal against the skin in this bodily region.

The inner volume 12 is preferably contoured so that none of the skin of the penis touches any portion of the device upon fitment of the lower lip portion 8 against the pubic bone area of the person using the device and application of reduced pressure to the interior volume of the device through hole 2. Thus, the device comprises a hole 20 at the flat bottom portion through which a flaccid penis is inserted prior to application of vacuum to the interior volume of the device.

Figure 2:
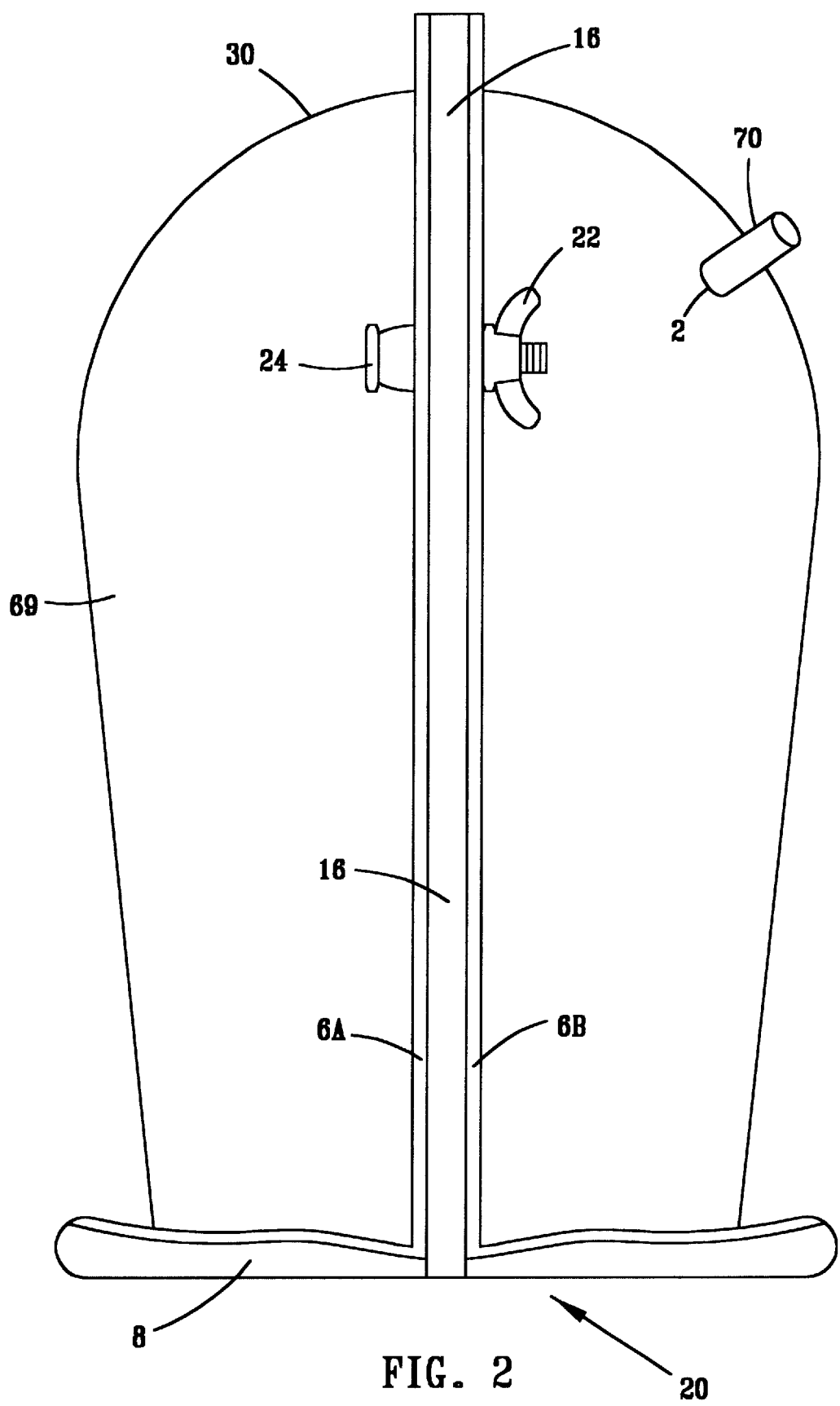
FIG. 2 is a side view of the device of the invention from FIG. 1 which has been rotated 90 degrees.

FIG. 2 is a side view of a device according to the invention from FIG. 1, which has been rotated 90 degrees to more clearly show the interface where the two members meet when the device is in a closed configuration. The lower lip portion 8 is shown as is the location of hole 20. A fastening means such as a wingnut 22 and bolt 24 are shown disposed through holes in each of the flange portions 6A and 6B of each of the members of the invention at the point of their coincidence. A gasket means 16 is disposed along the surface of at least one of the flange portions 6A or 6B to provide a vacuum-tight seal at the point of juncture of the two members when the device is in its closed configuration.

A vacuum fitting 70 is disposed in the hole 2 to provide a ready connection for the application of vacuum to the interior volume of the device.

Figure 3:
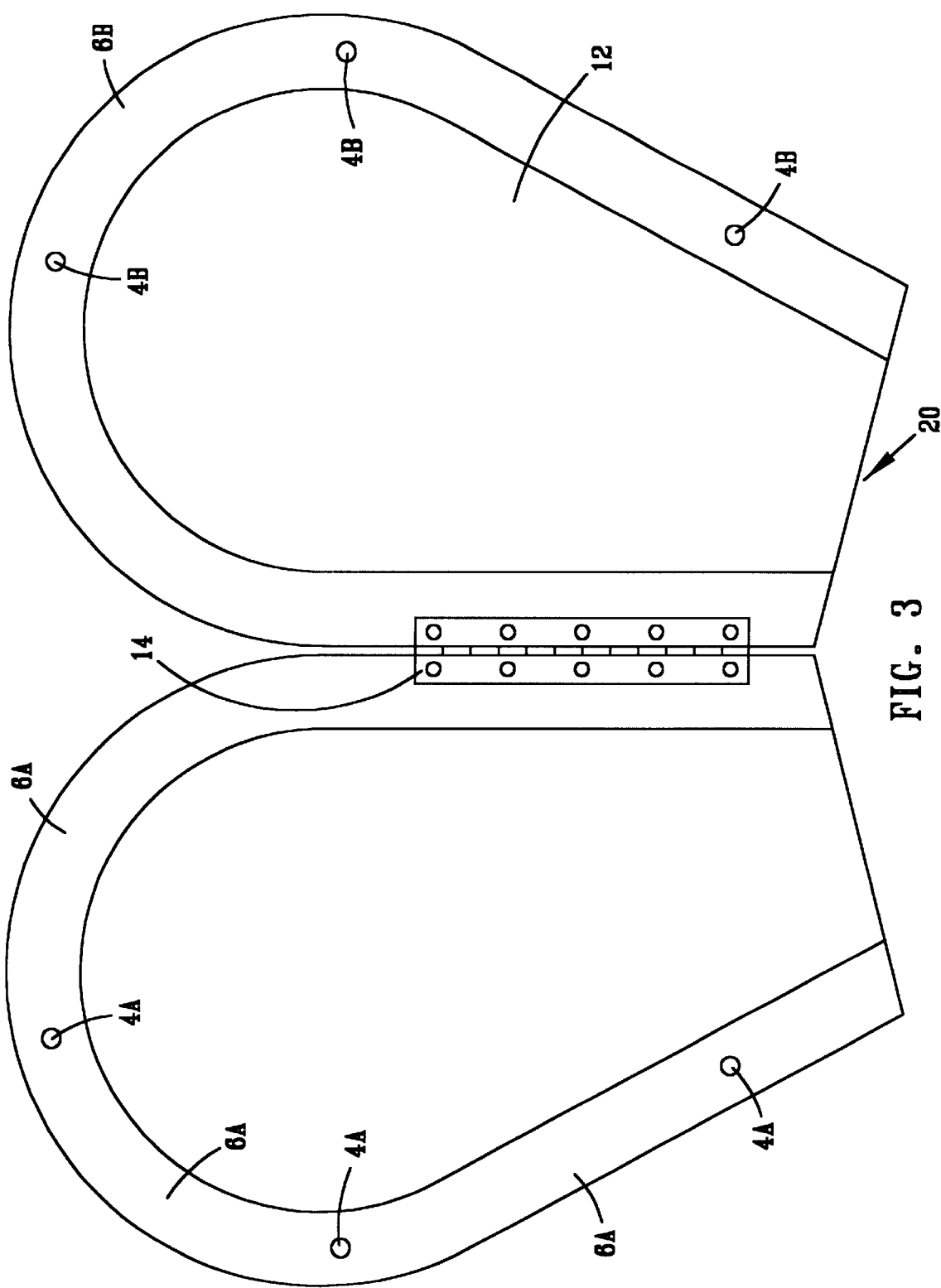
FIG. 3 is a side view of the device of the invention in its open configuration.

FIG. 3 shows a device according to the invention in its open configuration, and depicts the various elements of each of the members of the invention, including the flange portions of each member 6A and 6B upon at least one of which a gasket material is preferably disposed, a plurality of holes 4A and 4B, useful for maintaining the device in its closed position when such is desired, a flat lower portion 20, and the hinge means 14. The interior volume of one of the members 12 is also shown.

Figure 4:
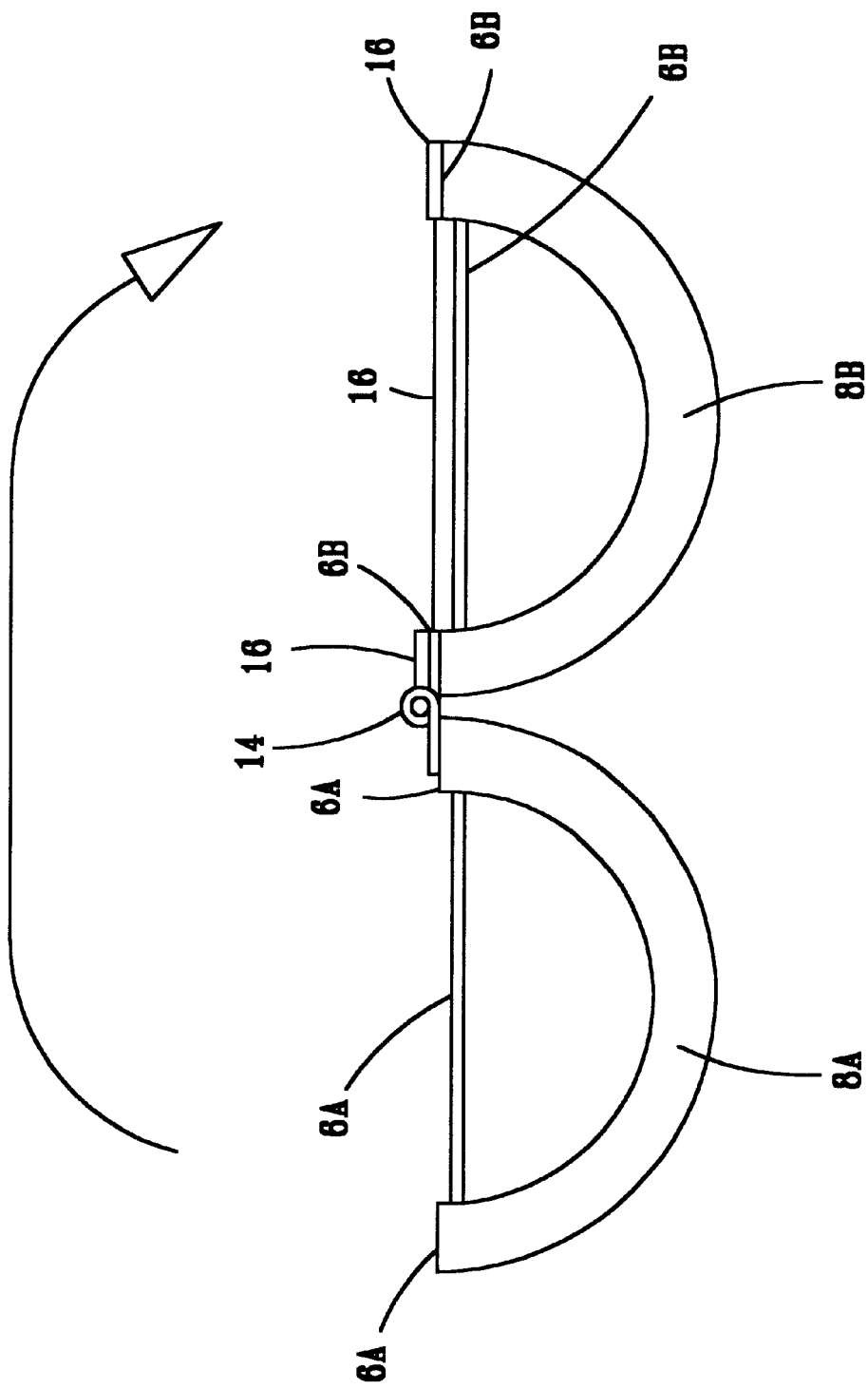
FIG. 4 is and end view of the device of the invention in its open configuration.

FIG. 4 shows the view from the bottom of a device according to the invention in its open configuration. Here, the portions 8A and 8B are shown which collectively comprise the lower lip portion 8 of the device when it is in its closed configuration, as is accomplished by closing the two members together as indicated by the arrows. The flanges 6A and 6B are shown, as is the gasket material 16 disposed on flange 6B and the hinge means 14.

Figure 5:
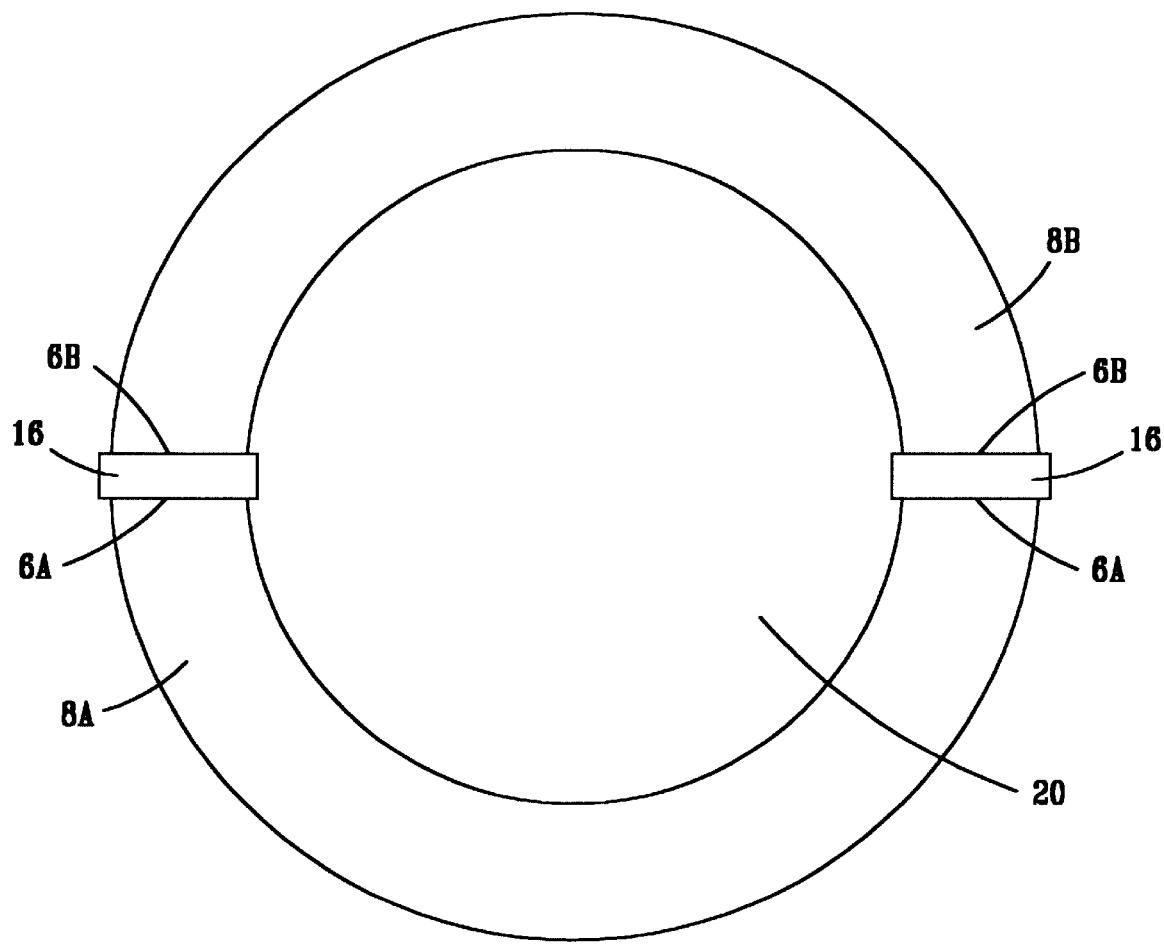
FIG. 5 is a view of the bottom of the device of the invention in its closed configuration.

FIG. 5 shows the view from the bottom of a device according to the invention in its closed configuration. Here, hole portion 20 through which a flaccid penis is inserted is depicted, as well as the orientation of the flange portions 6A and 6B with respect to the gasket means 16 and the sub portions 8A and 8B which collectively comprise lower lip portion 8 are shown.

It is most preferred that a device according to the invention be comprised of an inert polymeric material having no sharp edges since the device as a whole is designed to contact a sensitive area of the skin. Preferred materials of construction include plastics, such as polyolefins. halogenated polyolefins (such as PVC), polycarbonates, and polyacrylates. It is most preferred that a device according to the invention be constructed of a clear material, to permit the user to view the progress of the erection stimulation, and the most preferred material of construction is polymethylmethacrylate ("Plexiglass®").

Any suitable material known to be useful as a hinge means may be employed to join the members of the invention to one another. Preferably, the hinge means is a common hinge that comprises two flat pieces of steel or other rigid material which are joined together at a pivot point, as such is known to those skilled in the art. However, the invention contemplates other hinge means, such as a polypropylene bridge "cast-in" to the device or as a single construct, as hinges of polypropylene are well known in the art of polymers.

Various gasket materials may find use in the present invention for sealing the surfaces of the ip portions 6A and 6B to one another, as such materials are known to those skilled in the art, including paper. cork. rubber, foamed polymers, teflon®, etc. The primary requisite is that a vacuum tight seal be promoted by the presence of such gasket material.

The invention has been described as comprising a hole through the bulb-shaped surface of the invention to which a vacuum may be applied. Since it is desirable according to the invention to connect a source of vacuum to the device and to disconnect a source of vacuum to the device, it is convenient to employ two cooperatively connecting coupling portions as part of the vacuum conduit. Quick disconnect means for fluid communication are well known in the art, and any of such known means may be utilized in accordance with the invention. It is preferably to have a first connector of a pair of a cooperatively connecting pair physically attached to the hole in the bulb-shaped surface of the device. Through such means, all one must do is connect the source of vacuum (having the mate to the first connector attached to a vacuum hose, for example) to the connector for ease in vacuum connection.

Although the fastening means described herein comprises a bolt and wingnut pair, other functionally equivalent fasteners are herein indicated as being useful in this invention, including without limitation, hook and loop type fasteners (such as Velcro®), snaps, rivets, screws, etc., with the proviso that a device according to the invention is capable of being opened to permit the removal of an erection therefrom, or for cleaning purposes.

Use of a device according to the invention is straightforward. First, the members of the invention are closed with respect to one another (such as shown in FIGS. 1, 2, and 5) and a fastening means is engaged to hold the members in a closed position sufficient to permit the gasket means to form a vacuum-tight seal. Next, the device as a whole is placed over a flaccid penis with the lower lip portions 8A and 8B in contact with the pubic bone of the subject. Finally, a vacuum is applied to the inner volume of the device which surrounds the penis. By application of a vacuum in the range of between atmospheric pressure and 27 in. Hg, including every hundredth inch of mercury therebetween and more preferably a vacuum of between 5 and 10 in. Hg, a zone of reduced pressure can be caused to exist in the space surrounding the penis which causes blood from the body (which is at a higher pressure than inside the device) to be forced into the penis until the point is reached that no more blood may enter. At this point, the user may constrict the base of the penis to prevent the blood from flowing back out into the body, thus maintaining an erection long enough for insertion during a copulative act.

In an alternative method of use. a subject who does not normally have difficulty in achieving an erection may employ the device to achieve an erection on a repeated basis, for the purpose of causing the capacity of the penis to hold blood to increase, thus causing the penis to become enlarged over time. Accordingly, a device according to the invention may be used as a permanent penis-enlargement device.

One particular advantage of a device according to the invention is that it is contoured to prevent any portion of the skin of the penis from contacting the walls of the device. Thus increased growth potential of the penis may be realized over other devices in the prior art which permit the contact of the penis with surfaces of the devices. The instant invention contemplates the use of this principle to causing enlargement of other bodily parts, such as women's breasts, using members which are contoured to prevent contact between the skin of a breast and the walls of the device.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A device useful for causing an erection in human males, said device having a bulb-shaped outer surface and an interior volume, which comprises:
   a) a semi-bulbular first member comprising a semi-circular upper portion, a flat lower portion, and two straight sidewall portions, said sidewall portions angled inwardly from the semicircular upper portion and terminating at said flat lower portion, further comprising a horseshoe-shaped flange portion which circumscribes said sidewall portions and said semi-circular upper portion;
   b) a semi-bulbular second member comprising a semi-circular upper portion, a flat lower portion, and two straight sidewall portions, said sidewall portions angled inwardly from the semicircular upper portion and terminating at said flat lower portion, further comprising a horseshoe-shaped flange portion which circumscribes said sidewall portions and said semi-circular upper portion, wherein said first and said second members are hingably attached to one another along one of said sidewall portions of each member in such fashion to render said flange of said first member and said flange of said second member to contact one another upon closure of said first and said second members, and wherein said flat lower portions each comprise a lip portion shaped as a semicircle whose axis is perpendicular to the semi-circle of said semi-circular upper portion whereby a circular opening is formed at the lower portion of the device upon said closure, said circular opening being adapted to receive a flaccid penis.

2. A device according to claim 1 further comprising a fastening means for permitting said flange portion of said first member to be in contact with said flange portion of said second member so as to maintain an interface at which said flange portions coincide.

3. A device according to claim 1 to further comprising a gasket disposed on at least one of said flange portions.

4. A device according to claim 1 further comprising a means for applying a vacuum to the interior volume of said device.

5. A device according to claim 4 wherein said means for applying a vacuum comprises a hole disposed through said bulb shaped surface.

6. A device according to claim 1 further comprising a lip portion disposed at the flat lower portion, said lip portion contoured to substantially fit the pubic bone area of a human subject.

7. A process for causing enlargement of a penis comprising the steps of:
   a) providing a device having a bulb-shaped outer surface and an interior volume, which comprises:
      i) a semi-bulbular first member comprising a semi-circular upper portion, a flat lower portion, and two straight sidewall portions, said sidewall portions angled inwardly from the semicircular upper portion and terminating at said flat lower portion, further comprising a horseshoe-shaped flange portion which circumscribes said sidewall portions and said semi-circular upper portion;
      ii) a semi-bulbular second member comprising a semi-circular upper portion, a flat lower portion, and two straight sidewall portions, said sidewall portions angled inwardly from the semicircular upper portion and terminating at said flat lower portion, further comprising a horseshoe-shaped flange portion which circumscribes said sidewall portions and said semi-circular upper portion, wherein said first and said second members are hingably attached to one another along one of said sidewall portions of each member in such fashion to render said flange of said first member and said flange of said second member to contact one another upon closure of said first and said second members, and wherein said flat lower portions each comprise a lip portion shaped as a semicircle whose axis is perpendicular to the semi-circle of said semi-circular upper portion whereby a circular opening is formed at the lower portion of the device upon said closure, said circular opening being adapted to receive a flaccid penis;
   b) effecting closure of said first member and said second member;
   c) providing a non-erect penis;
   d) inserting the non-erect penis into said circular opening; and
   e) applying a vacuum to said interior volume in an effective amount for causing the non-erect penis to increase in size by virtue of the pressure differential existing between said interior volume and the ambient pressure.

8. A process according to claim 7 wherein said vacuum is in the range of between 5.00 inches of mercury and 27.00 inches of mercury, including every hundredth inch therebetween.

9. A process according to claim 7 further comprising the steps of:
   e) causing the pressure inside of said interior volume to return to ambient pressure; and
   f) repeating step d).

10. A process according to claim 9 wherein steps (e) and (f) are repeated until the penis has reached full erection.

* * * * *